(12) United States Patent
Roach et al.

(10) Patent No.: US 10,881,471 B2
(45) Date of Patent: Jan. 5, 2021

(54) COOLING A SURGICAL ROBOT ARM

(71) Applicant: CMR Surgical Limited, Cambridge (GB)

(72) Inventors: Christopher James Roach, Wisbech (GB); Nikki Priyam Su-Ling Phoolchund, Cambridge (GB); Paul Christopher Roberts, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 61 days.

(21) Appl. No.: 16/193,767

(22) Filed: Nov. 16, 2018

(65) Prior Publication Data

US 2019/0083182 A1  Mar. 21, 2019

Related U.S. Application Data

(63) Continuation of application No. PCT/GB2017/051306, filed on May 11, 2017.

(30) Foreign Application Priority Data

May 19, 2016 (GB) .................................. 1608818.9

(51) Int. Cl.
*A61B 34/30* (2016.01)
*B25J 19/00* (2006.01)
(Continued)

(52) U.S. Cl.
CPC .............. *A61B 34/30* (2016.02); *A61B 46/10* (2016.02); *B25J 19/0054* (2013.01);
(Continued)

(58) Field of Classification Search
CPC .................... A61B 34/30; A61B 46/10; A61B 2018/00023; A61B 2034/302; B25J 19/0083; B25J 19/0054
See application file for complete search history.

(56) References Cited

U.S. PATENT DOCUMENTS

2013/0345862 A1  12/2013  Schlaich et al.

FOREIGN PATENT DOCUMENTS

GB  2532719 A  *  6/2016  ............. A61B 46/10
GB  2532719 A     6/2016
(Continued)

OTHER PUBLICATIONS

International Search Report and Written Opinion of PCT/GB2017/051306 dated Sep. 11, 2017, 13 pages.

*Primary Examiner* — Rex R Holmes
(74) *Attorney, Agent, or Firm* — Rothwell, Figg, Ernst & Manbeck, P.C.

(57) ABSTRACT

A cooling structure and a method of cooling a surgical robot arm. The surgical robot arm extends from a proximal end attached to a base to a distal end attachable to a surgical instrument via a series of links interspersed by articulations. The cooling structure comprises a loop for circumscribing the surgical robot arm. The loop comprises a hollow interior for feeding cooling fluid through the loop, and a series of orifices directed towards the surgical robot arm for feeding cooling fluid from the loop towards the surgical robot arm. The cooling structure further comprises a feeder conduit attached to the loop for feeding cooling fluid from a cooling fluid source to the loop.

18 Claims, 7 Drawing Sheets

(51) Int. Cl.
*A61B 46/10* (2016.01)
*A61B 18/00* (2006.01)

(52) U.S. Cl.
CPC . *B25J 19/0083* (2013.01); *A61B 2018/00023* (2013.01); *A61B 2034/302* (2016.02)

(56) References Cited

FOREIGN PATENT DOCUMENTS

| | | | |
|---|---|---|---|
| JP | 04372390 A | * | 12/1992 |
| JP | H04372390 A | | 12/1992 |
| JP | P3376678 B2 | | 2/2003 |

* cited by examiner

COOLING A SURGICAL ROBOT ARM

The present application is a continuation of PCT Application No. PCT/GB2017/051306 filed May 11, 2017, which claims the benefit priority to GB Application No. 1608818.9 filed May 19, 2016, the entire contents of each of which are hereby incorporated by reference for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

A surgeon utilises many instruments during the course of a typical laparoscopy operation. For this reason, it is desirable for the instruments to be detachable from and attachable to the end of the robot arm mid-operation. Both when detaching and attaching an instrument, the operator places a hand on the robot arm to support it. Safety regulations set maximum temperature limits of surfaces in the operating theatre which are allowed to be contacted by people. The maximum temperature limits depend on the length of time of the contact. For example, the current maximum temperature limit set by the medical electrical equipment and systems standard BS EN 60601 for a surface in the operating theatre which is able to be touched by an operator for up to 1 minute is 48° C. (see page 183, table 23).

During use, the motors located in the robot arm which drive movement of the robot arm and the instrument generate heat. If the robot arm is shrouded in a drape, then that generated heat is mostly retained in the vicinity of the robot arm causing the temperature of the surface of the robot arm to increase. The temperature of the surface of the arm is also dependent on the ambient temperature of the operating theatre.

In order to ensure that the temperature regulations are met regardless of the ambient temperature and the length and intensity of the robot arm manipulation during the procedure, it is desirable to cool the robot arm during use. It is desirable that this cooling be achieved in a manner which does not interfere with the manipulation of the robot arm. Additionally, it is desirable that the cooling apparatus is quick and easy to setup and remove, and otherwise as unobtrusive as possible to the operating theatre staff.

SUMMARY OF THE INVENTION

According to an aspect of the invention, there is provided a cooling structure for cooling a surgical robot arm, the surgical robot arm extending from a proximal end attached to a base to a distal end attachable to a surgical instrument via a series of links interspersed by articulations, the cooling structure comprising: a loop for circumscribing the surgical robot arm, the loop comprising: a hollow interior for feeding cooling fluid through the loop, and a series of orifices directed towards the surgical robot arm for feeding cooling fluid from the loop towards the surgical robot arm; and a feeder conduit attached to the loop for feeding cooling fluid from a cooling fluid source to the loop.

The series of orifices may comprise orifices directed towards the distal end of the surgical robot arm. The series of orifices may comprise orifices directed away from the distal end of the surgical robot arm.

The loop may have a uniform cross-section. The loop may be a continuous closed loop. The loop may be a discontinuous closed loop.

The cooling structure may further comprise biasing projections attached to the loop, the biasing projections being directed towards the surgical robot arm, the biasing projections configured to contact the surgical robot arm so as to space the loop from the surgical robot arm. The biasing projections may comprise leaf springs.

The cooling structure may further comprise one or more fasteners configured to fasten the cooling structure to the surgical robot arm.

The cooling structure may further comprise one or more further loops for circumscribing the surgical robot arm, each further loop comprising: a hollow interior for feeding cooling fluid through the further loop, and a series of further orifices directed towards the surgical robot arm for feeding cooling fluid from the further loop towards the surgical robot arm.

The feeder conduit may be attached to each further loop for feeding cooling fluid to that further loop, wherein the feeder conduit spaces the loop and the one or more further loops apart from each other.

The cooling structure may be collapsible into a storage configuration in which the loop and the one or more further loops stack together.

According to an aspect of the invention, there is provided a sterile drape for draping over a surgical robot arm comprising the cooling structure of any preceding claim.

The loop and the one or more further loops may be separated by portions of drape. The loop may join together detached drape portions.

According to an aspect of the invention, there is provided a surgical robot system comprising: a surgical robot arm extending from a proximal end attached to a base to a distal end attachable to a surgical instrument via a series of links interspersed by articulations; and a cooling structure.

The loop may circumscribe the distal end of the surgical robot arm.

The loop or one of the one or more further loops may circumscribe an articulation of the surgical robot arm.

The surgical robot arm may further comprise one or more complimentary fasteners configured to fasten to the one or more fasteners of the cooling structure.

According to an aspect of the invention, there is provided a method of cooling a surgical robot arm, the surgical robot arm extending from a proximal end attached to a base to a distal end attachable to a surgical instrument via a series of links interspersed by articulations, the method comprising: forcing cooling fluid from a cooling fluid source through a feeder conduit to a loop which circumscribes the surgical robot arm; and feeding the cooling fluid through a hollow interior of the loop and through a series of orifices directed towards the surgical robot arm.

The method may further comprising extracting cooling fluid from the interior of the surgical robot arm.

The method may further comprise applying differential pressures to the cooling fluid forced into the feeder conduit and the cooling fluid extracted from the interior of the surgical robot arm.

The cooling fluid may be ambient air. The cooling fluid may be bottled gas.

BRIEF DESCRIPTION OF THE FIGURES

The present invention will now be described by way of example with reference to the accompanying drawings. In the drawings.

DETAILED DESCRIPTION

Figure 3:
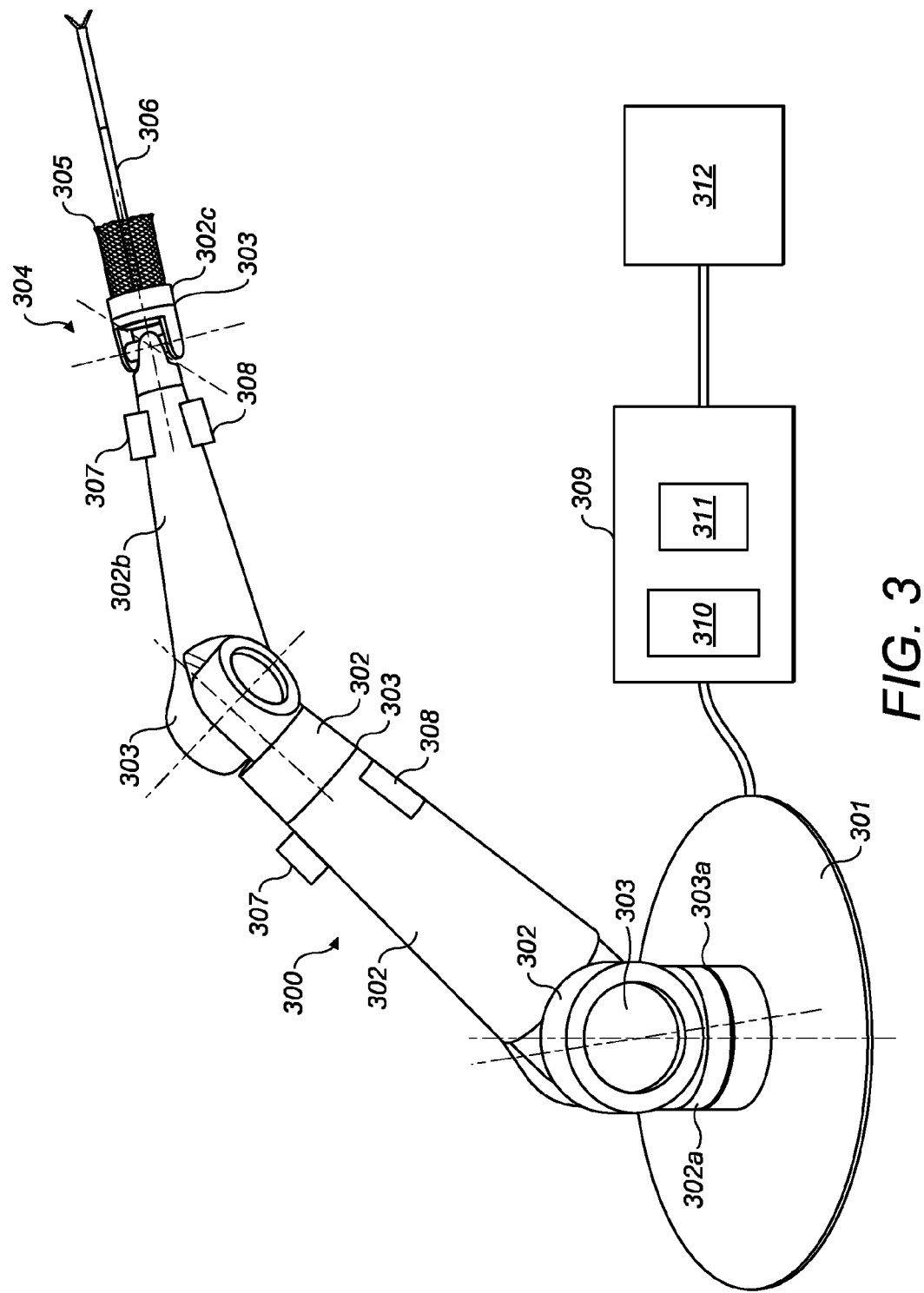
FIG. 3 illustrates a surgical robot.

FIG. 3 illustrates a surgical robot having an arm 300 which extends from a proximal end attached to a base 301. The arm comprises a number of rigid links 302. The links are coupled by revolute joints 303. The most proximal link 302a is coupled to the base by joint 303a. It and the other links are coupled in series by further ones of the joints 303. Suitably, a wrist 304 is made up of four individual revolute joints. The wrist 304 couples one link (302b) to the most distal link (302c) of the arm. The most distal link 302c is at the distal end of the arm and carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 1:
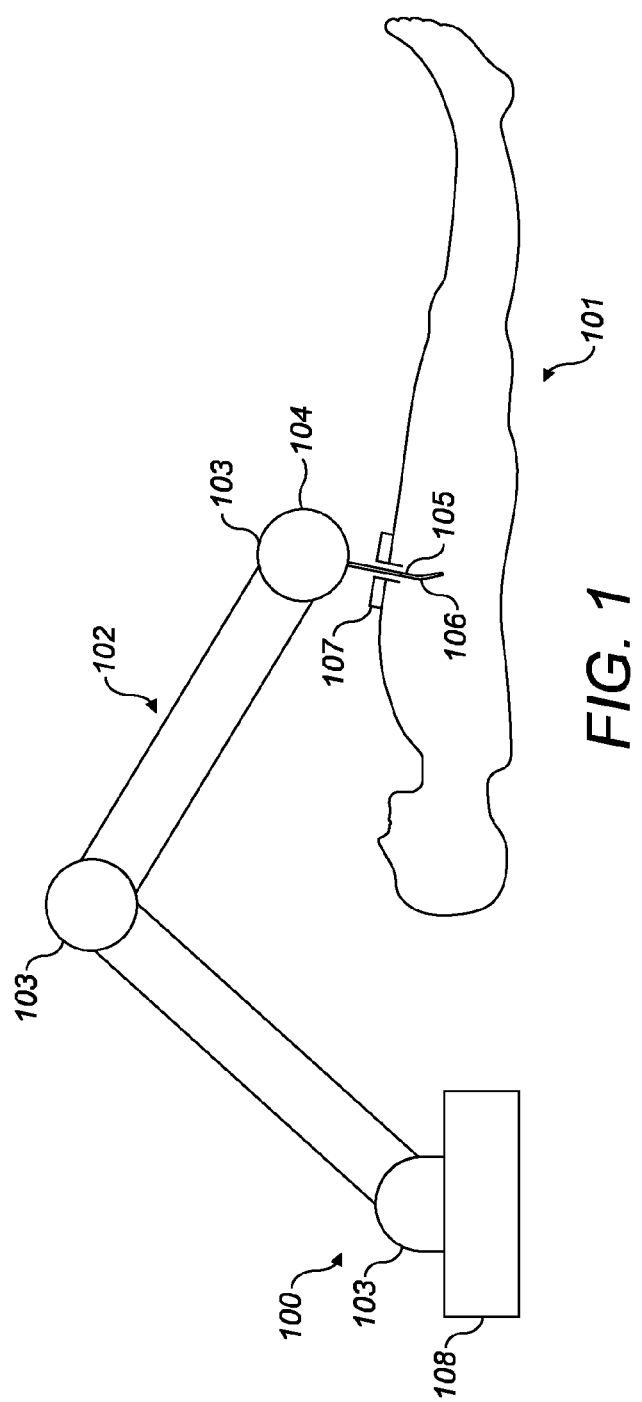
FIG. 1 illustrates a surgical robot performing a surgical procedure.
Figure 2:
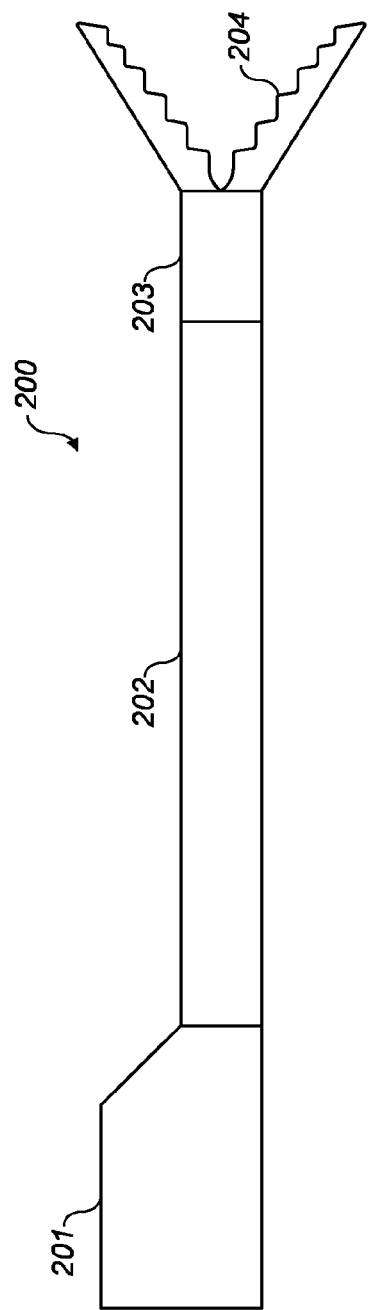
FIG. 2 illustrates a known surgical instrument.

The arm terminates in an attachment 305 for interfacing with the instrument 306. Suitably, the instrument 306 takes the form described with respect to FIG. 2. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 309. A control unit 309 comprises a processor 310 and a memory 311. Memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
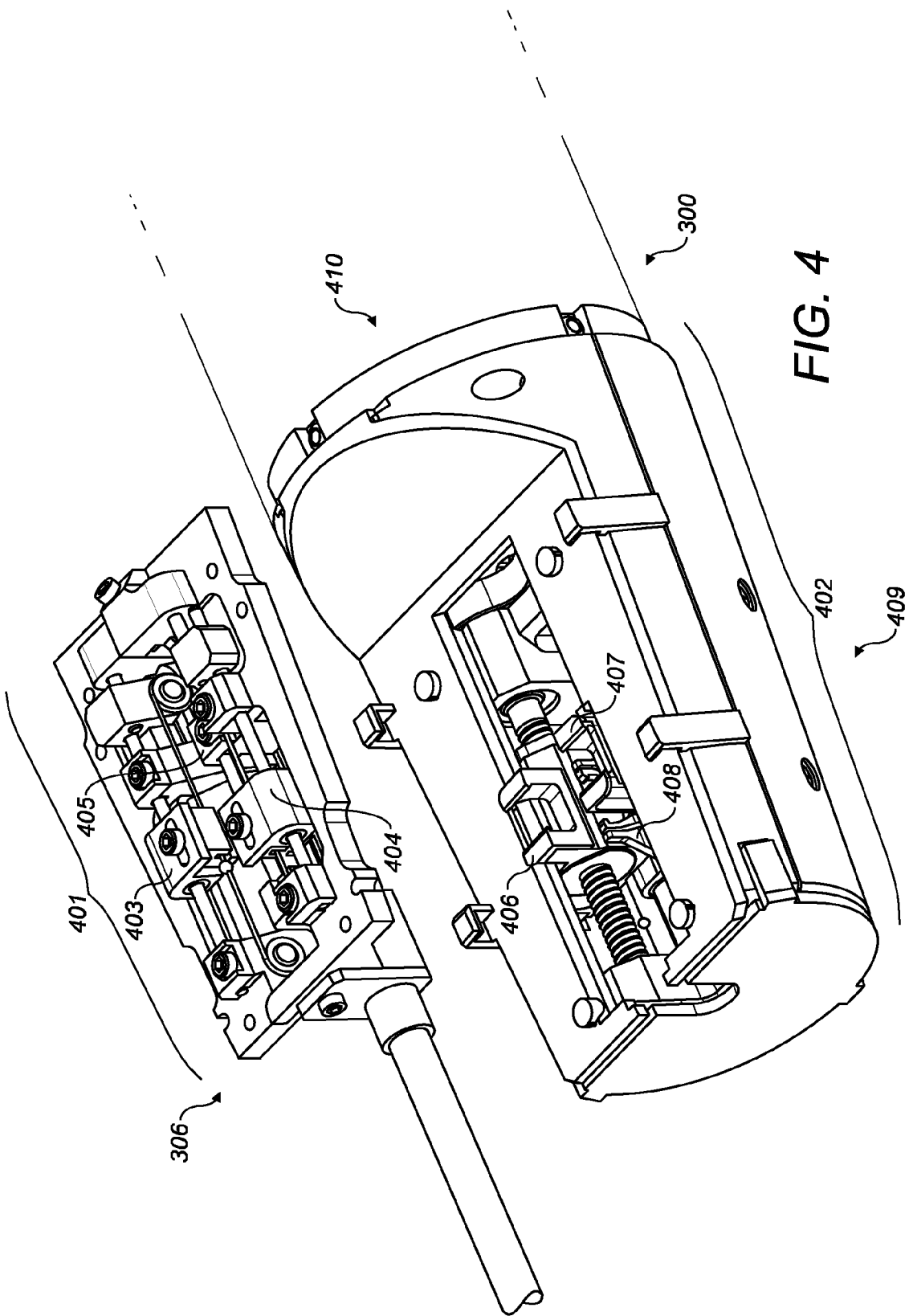
FIG. 4 illustrates the instrument being positioned into engagement with the robot arm.

FIG. 4 illustrates an instrument 306 being placed into engagement with the robot arm 300. The instrument interface 401 comprises instrument interface elements 403, 404 and 405 which mechanically interconnect with corresponding interface elements 406, 407 and 408 of the drive assembly 402 in order to transfer drive from the robot arm to the instrument. Typically, when engaging or disengaging the instrument with the robot arm, the operator holds the robot arm in the vicinity of the drive assembly. For example, the operator may hold the base 409 of the drive assembly or the portion of the arm 410 next to the drive assembly. Thus, it is desirable that the temperature of this portion of the robot remain below the maximum temperature limit set by the regulatory authorities.

Figure 5:
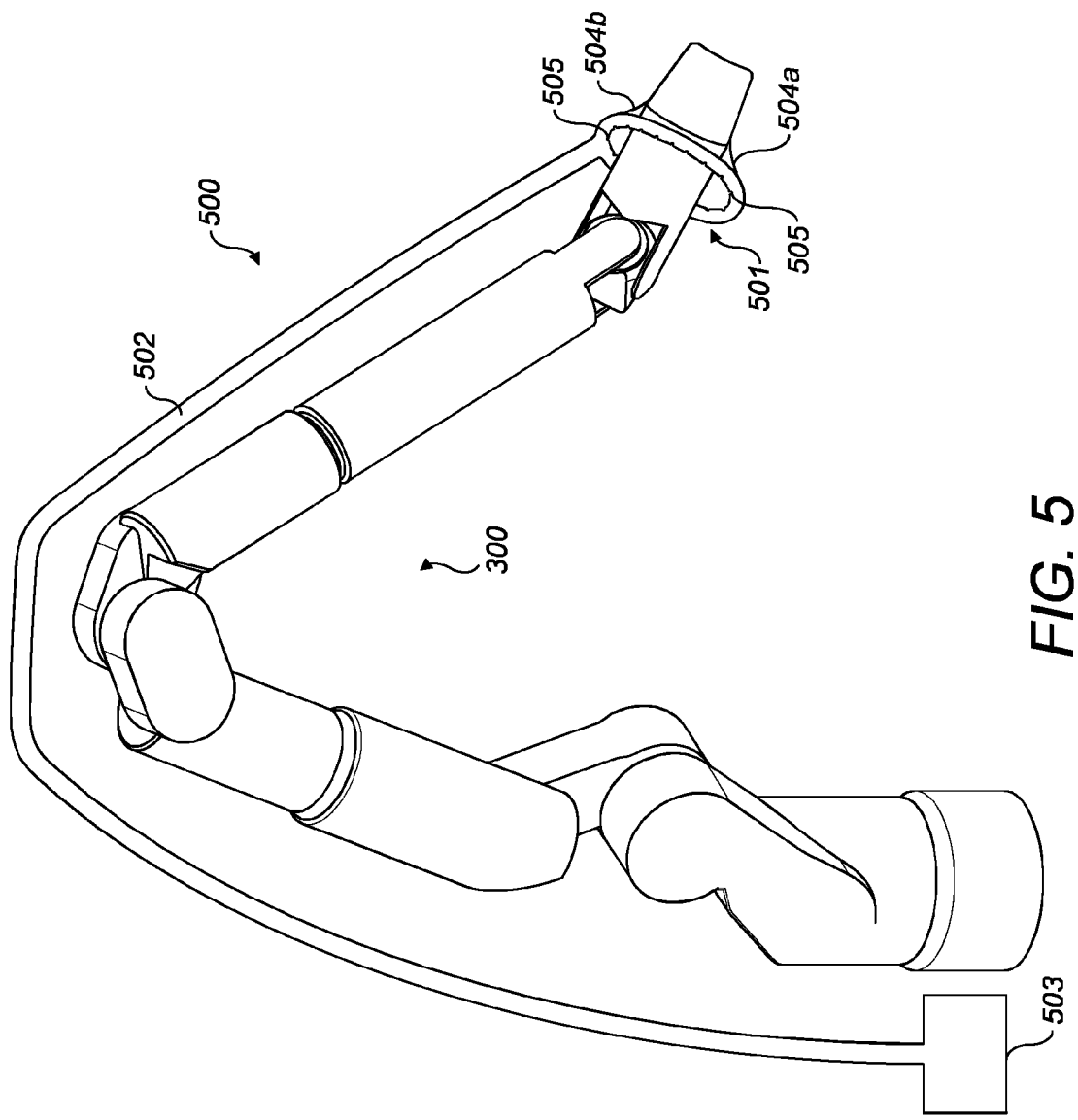
FIG. 5 illustrates a cooling structure for cooling a surgical robot arm.

FIG. 5 illustrates a cooling structure 500 for cooling a surgical robot arm 300. The cooling structure 500 is illustrated in a configuration in which it is mounted to the robot arm 300. The cooling structure 500 is detachable from the robot arm. The cooling structure comprises a loop 501 and a feeder conduit 502. A cooling fluid source 503 is attachable to the feeder conduit 502. The feeder conduit 502 is shaped so as to be capable of feeding cooling fluid from the cooling fluid source 503 to the loop 501. For example, the feeder conduit 502 may be a hollow tube. The loop 501 circumscribes the robot arm. The loop 501 surrounds the robot arm in the cross-sectional plane of the robot arm. The loop has a hollow interior so as to be capable of feeding cooling fluid through the loop.

The loop has a series of orifices 505. These orifices are openings in the outer surface of the loop which go through to the hollow interior of the loop. In other words, they are through holes. Cooling fluid inside the loop passes through these orifices to the exterior of the loop. Thus, the orifices are bleed holes for the cooling fluid. The orifices are directional. They enable the cooling fluid to be aimed in particular directions. Suitably, the orifices are directed towards the robot arm in order to feed cooling fluid from the loop towards the robot arm.

The constituent parts of the cooling structure are sized and shaped so as to aid distribution of cooling fluid to the desired arm locations during manipulation of the arm during surgery. Since the arm is being articulated throughout the operation, the rotational position of the loop with respect to the arm is generally not known. Thus, the conduit, loop and orifices are each individually sized and shaped so as to distribute cooling fluid evenly through the orifices of the loop. In that way, the portion of the arm adjacent to the loop is evenly cooled by virtue of the cooling fluid emitted from the orifices.

The loop may have a uniform cross-section. For example, the loop may have a circular cross-section. Suitably, the loop is of a uniform shape. For example, the loop may be a ring. The ring may be circular. A uniform cross-section and uniform shape of the loop ensures the cooling fluid is at a uniform pressure throughout the interior of the loop, and hence ensures that the pressure of the cooling fluid escaping from the loop is uniform around the loop. The orifices may be regularly spaced around the surface of the loop facing the robot arm. Alternatively, the orifices may be arranged around the surface of the loop facing the robot arm so as to only be located on those parts of the loop which are directed to the portion of the robot arm which is to be cooled.

The loop may be located relative to the robot arm such that it directs the cooling fluid towards a part of the robot arm that is likely to be handled by a person. For example, the loop may circumscribe the distal end of the robot arm. This enables the loop to direct cooling fluid over the distal end of the robot arm. The operator holds the distal end of the robot arm whilst detaching/attaching an instrument. The operator may also hold the distal end of the robot arm during initial set-up of the robot prior to the beginning of an operation. The loop may circumscribe a joint of the robot arm. In some selectively compliant operating modes, an operator is able to push a joint of the robot arm to cause it to move without changing the position of the end effector. For example, an operator may be able to push an elbow joint of the arm to cause it to move out of their way. Thus, the loop may circumscribe the elbow joint to direct cooling fluid over it. The loop may be located relative to the robot arm such that it directs the cooling fluid towards a part of the robot arm that is likely to increase in temperature. For example, the loop may circumscribe a portion of the arm housing a motor or a motor driver or other electronics.

The orifices of the loop may be located on the loop so as to direct the cooling fluid towards the part of the robot arm that is likely to be handled by a person. The operator typically handles the underside of the drive assembly 402 and/or the arm portion 410 next to the drive assembly when changing instruments. The arm portion 410 may increase in temperature during use of the robot arm relative to the ambient temperature of the operating theatre. If the loop is to cool the part of the robot arm that an operator holds whilst changing instruments, then the loop may be located over the arm portion 410 of the robot arm that is next to the drive assembly 402. In this example, the orifices of the loop may all be located in a direction pointing towards the distal end of the robot arm. Thus the cooling fluid that escapes from the loop is all directed towards the part of the robot arm (402, 410) that the operator touches. In another example, the operator may be likely to handle the surface of the robot arm on both sides of the loop. In this case, some orifices may be located in a direction pointing towards the distal end of the robot arm, and some orifices may be located in a direction pointing away from the distal end of the robot arm.

The cooling structure of FIG. 5 has biasing projections 504a, 504b attached to the loop. Each biasing projection is directed towards the robot arm, and is configured to contact the robot arm so as to space the loop from the robot arm. The biasing projections thus support the loop. They prevent the loop from directly contacting the robot arm. They thus prevent the loop from hindering movement of the robot arm. Suitably, there are at least two biasing projections per loop. There may be more than two biasing projections per loop. Each biasing projection may take any suitable form, for example a leaf spring.

The cooling structure may further comprise one or more fasteners for fastening the cooling structure to the robot arm. These fasteners may be located on any one or all of the loop 501, the feeder conduit 502, and the biasing projections 504a, 504b. Each biasing projection 504a, 504b may be a fastener. The fasteners fasten to complimentary-shaped fasteners on the robot arm. For example, the fastener on the cooling structure may be a clip which fastens to a complimentary-shaped recess in the surface of the robot arm. The fasteners may take any suitable form, for example clips, clasps, buckles, latches, plugs, sockets, hooks, eyes, poppers, eyelets, buttons, Velcro as long as they are capable of secure the cooling structure to the arm whilst the arm is being manipulated.

Figure 6:
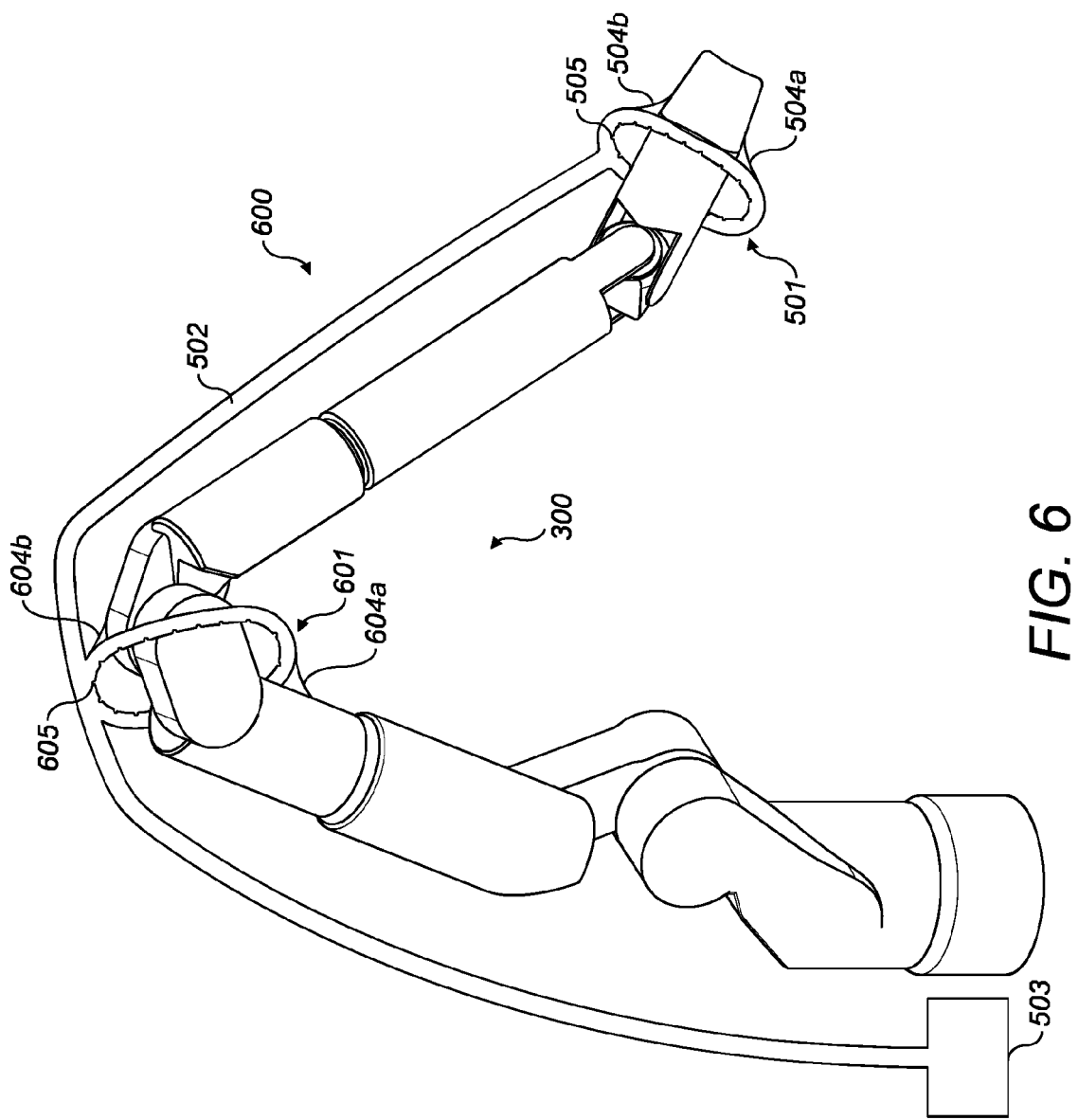
FIG. 6 illustrates a cooling structure for cooling a surgical robot arm.

FIG. 6 illustrates a further cooling structure 600 for cooling a surgical robot arm 300. The cooling structure 600 is illustrated in a configuration in which it is mounted to the robot arm 300. The cooling structure 600 is detachable from the robot arm. The cooling structure 600 is the same as the cooling structure 600 of FIG. 5 except that in addition to the loop 501, the cooling structure 600 has a further loop 601. Further loop 601 may take any of the forms described in respect of loop 501 above. The cooling structure 600 further comprises biasing projections 604a, 604b for spacing the loop 601 from the robot arm. Biasing projections 604a, 604b may be as described above in respect of biasing projections 504a, 504b. The cooling structure may comprise further fasteners attached to loop 601 or biasing projections 604a, 604b to secure the cooling structure to the robot arm.

Further loop 601 circumscribes the robot arm in a different location to that at which loop 501 circumscribes the robot arm. Suitably, both loops circumscribe the robot arm in locations which cause their orifices to direct cooling fluid towards part of the robot arm which is likely to be handled by a person and/or which is likely to increase in temperature during manipulation of the arm. In FIG. 6, loop 501 circumscribes the distal end of the robot arm next to where the operator holds the robot arm in order to change instruments. Loop 601 circumscribes the elbow of the robot arm which the operator may touch during an operation in order to move it in a selectively compliant operating mode of the robot arm. The orifices 605 on loop 601 point towards the robot arm. Suitably, some of these orifices point towards the distal end of the arm and some of these orifices point towards the proximal end of the arm. Thus, cooling fluid is directed all over the elbow joint, thus ensuring the elbow joint is sufficiently cool all over for human contact.

Loop 501 and loop 601 are spaced apart. They are connected to each other by the feeder conduit 502. Feeder conduit 502 is attached to each loop 501, 601 for feeding cooling fluid to that loop from the cooling fluid source 503. The feeder conduit 502 acts to space the loops 501, 601 apart. Alternatively, loop 601 may be fed by a different feeder conduit to the feeder conduit that feeds loop 501. The two feeder conduits may be joined distal of the loops 501 and 601 such that they share a common attachment to the cooling fluid source 503. Alternatively, the two feeder conduits may each be independently attached to the cooling fluid source 503.

Although FIG. 6 illustrates two loops 501 and 601, any number of further loops may be included in the cooling structure. Each further loop is shaped and configured as described with respect to loops 501 and 601.

Figure 7:
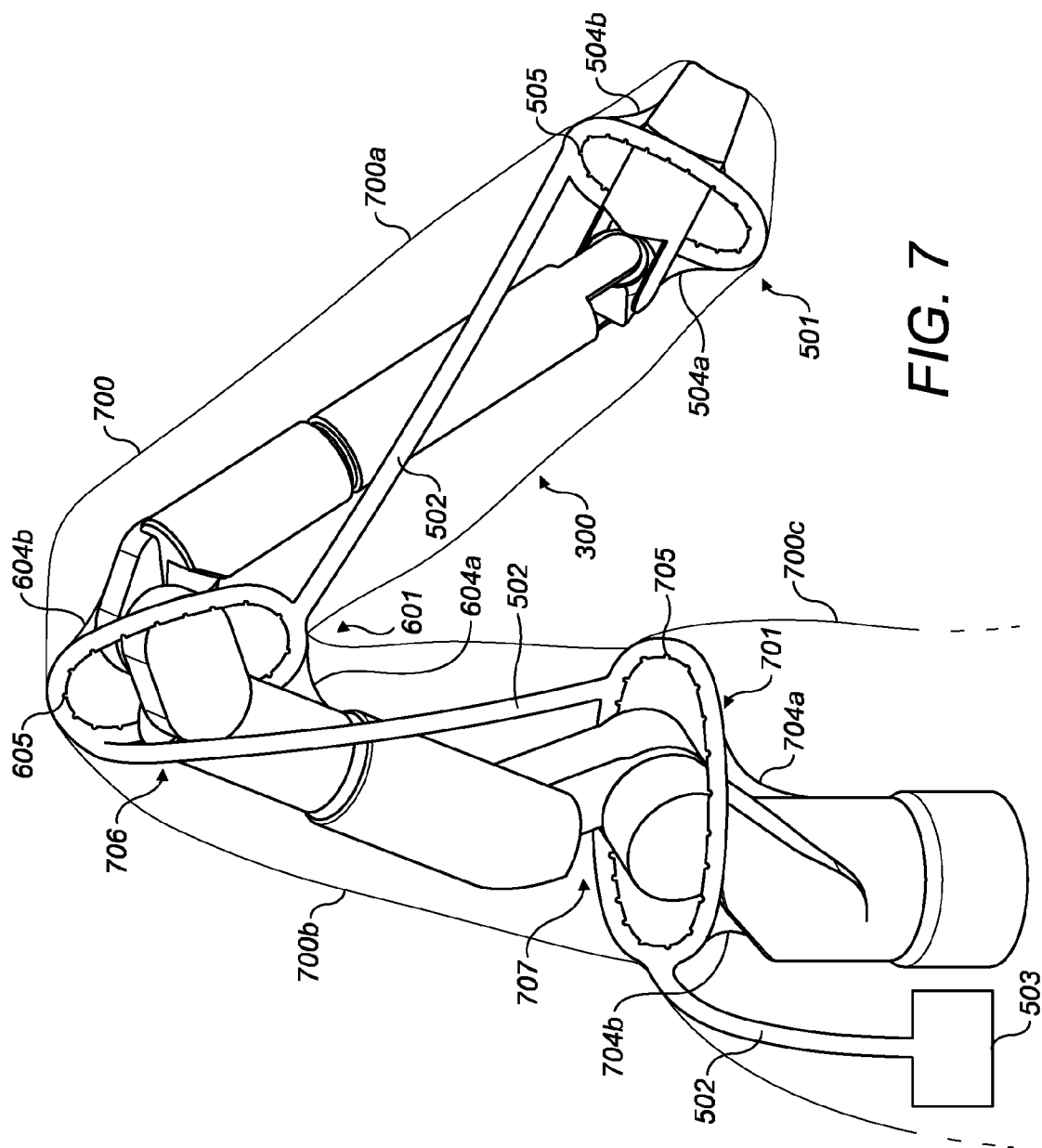
FIG. 7 illustrates a sterile drape with an integrated cooling structure.

FIG. 7 illustrates a sterile drape 700 for covering the robot arm 300. The sterile drape provides a sterile barrier between the non-sterile robot arm and the sterile operating theatre. The sterile drape 700 incorporates a cooling structure for cooling the robot arm. The sterile drape 700 may incorporate any of the cooling structures described herein. In the example shown in FIG. 7, the sterile drape incorporates a cooling structure which includes three loops 501, 601, 701 each of which has orifices 505, 605, 705 configured to emit cooling fluid in the direction of the robot arm. Feeder conduit 502 is incorporated into the drape. For example, feeder conduit 502 may be a fluid drainage channel within the drape. Feeder conduit 502 feeds cooling fluid to each loop 501, 601, 701. FIG. 7 illustrates the drape 700 mounted to the robot arm 300. The drape 700 is detachable from the robot arm.

The loops 501, 601 and 701 are separated by portions of the drape 700. The loops may be located so as to circumscribe joints of the robot arm. For example, in FIG. 7, loop 601 surrounds the elbow joint 706 of the robot arm and loop 701 surrounds the shoulder joint 707 of the robot arm. The loops are incorporated into the surface of the drape. Thus, together with their biasing projections, the loops act to space the drape from the robot arm. By locating the loops so as to surround joints of the robot arm, those loops space the fabric of the drape from the joints. Thus, the loops prevent the fabric of the drape from getting caught in the joints as the robot arm is manipulated. The loops may be rigidly connected to the drape material surrounding them. Alternatively, the loops may be moveably connected to the drape material surrounding them. For example, the drape may be able to rotate relative to the loops. This rotation may be such that the drape rotates relative to each loop about the longitudinal axis of the part of the arm proximal to the loop. In other words, the drape rotates relative to each loop about the roll axis of the arm proximal to the loop.

The cooling structure may be collapsible into a storage configuration in which the loops stack together. Suitably, the feeder conduit is flexible to enable the cooling structure to collapse into the stacking formation. The feeder conduit may connect the loops together in a manner which aids the collapse. For example, in FIG. 7, the feeder conduit connects one side of one loop to an opposing side of the next loop. Twisting adjacent loops in opposing directions causes the feeder conduit to collapse in a spiral shape, thereby enabling the loops to stack together. If the cooling structure forms part of the drape, then the drape collapses with the cooling structure into the stacked formation.

The drape may be manufactured and packaged as a single component with the cooling structure integral to the drape. The one or more loops may aid shrouding the robot arm with the drape. The drape is applied to the distal end of the robot arm and pulled over the robot arm until the drape reaches the robot arm base. The operator can apply the stacked drape directly to the distal end of the robot arm, and then unfold the drape one stacked loop at a time. As each stacked loop is unfolded, the drape covers more of the robot arm. Thus, the drape is shrouded over the robot arm quickly and easily. The likelihood of tearing the drape is reduced because the operator is not directly pulling the fabric of the drape itself in order to cover the robot arm. Suitably, the loops comprise tabs, for example ring pulls. In this case, the operator unfolds the stacked loops by grasping each loop in turn by its tabs and pulling the tabs over the robot arm.

Alternatively, the drape may be manufactured and packaged as separate components. For example, there may be two or more detached drape portions. A loop joins together detached drape portions. The loop may seal the detached drape portions together by any suitable means which maintains the sterile barrier. For example, the loop may seal the detached drape portions together using a press-seal. The operator may attach the drape portions together as the drape is applied to the robot arm. Taking the arrangement shown in FIG. 7 as an example, the drape may be packaged in three sections. The first section includes the cooling structure and the first drape portion 700a. The first drape portion joins loops 501 and 601. The second section includes the second drape portion 700b. The third section includes the third drape portion 700c. The operator applies the first section to the robot arm by unstacking the loops of the cooling structure as previously described. The operator then pulls the second drape portion over the robot arm and secures it to the loop 601 at one end and the loop 701 at the other end. The operator then pulls the third drape portion over the robot arm and secures it to the loop 701 at one end. A single component drape is bulky and hence cumbersome to unfold over the robot arm in one go. By applying the drape in portions as described here, the drape is easier to manage.

In implementations in which the drape is applied in portions to the robot arm, the loops are located in those places where the drape is demountable. The shape of the drape may be different in the different portions. For example, the portion of the drape that covers the distal end of the robot arm may be narrower in diameter than the remainder of the drape and/or taper toward the terminal link of the robot arm. This portion of the drape may be tubular. The portion of the drape that covers the proximal end of the robot arm may be wider in diameter than the remainder of the drape. This portion of the drape may be conical. By tailoring the size of the drapes of the different portions, a closer-fit of the drape on the robot arm is achieved, whilst still preventing the drape from interfering with the manipulation of the arm. FIG. 7 illustrates three loops and three drape portions 700a, 700b, 700c. Further loops and drape portions may be used.

The preceding paragraphs describe implementations in which the loops provide structural support to the drape in addition to providing a path for the cooling fluid. In each of these implementations one or more further loops may be used which provide structural support to the drape only. These loops do not provide a path for the cooling fluid. These loops may take the same shape and form as the loops described herein, modified in that they do not have orifices. The loops circumscribe the arm as previously described. The one or more further loops may be attached to the cooling fluid conduit. This is to aid the positioning of the one or more further loops only. There is no fluid path between the cooling fluid conduit and the one or more further loops. Alternatively, the one or more further loops may be attached to one or more further conduits which themselves are not cooling fluid paths. These one or more further conduits have the same shape and form as the other conduits described herein.

The cooling structure may be used according to the following method. The cooling structure is connected to the cooling fluid source. The cooling fluid may be ambient air which is pressurised into the cooling structure. The cooling fluid may be bottled gas which cools via the adiabatic expansion effect when applied into the cooling structure. The cooling fluid may be a liquid. For example, the cooling fluid may be water.

The cooling fluid is forced into the feeder conduit of the cooling structure from the cooling fluid source. The cooling fluid feeds through the feeder conduit to the one or more loops. The cooling fluid feeds through the loops and escapes from the loops via the orifices of the loops in a direction towards the surface of the robot arm. The surface of the robot arm is thereby cooled. The cooling fluid return path may be through the interior of the arm back to the base of the robot. Alternatively, the cooling fluid return path may be between the robot arm and the drape back to the base of the robot.

The cooling fluid may be forced into the feeder conduit with a positive pressure of less than 1 bar. Suitably, the pressure is positive and less than or the same as 100 mbar. This provides sufficient cooling of the robot arm to meet the safety regulations. The cooling fluid may be extracted once it has been expelled from the orifices of the loops. This extraction may be forced by sucking the cooling fluid. Alternatively, the extraction may be non-forced. In other words, the extraction may be allowed to happen naturally. A differential pressure system may be applied. In this case, the pressure at which the cooling fluid is forced in to the feeder conduit is selected in dependence on the pressure at which the cooling fluid is fed back so as to maintain the desired pressure difference. For example, this pressure difference may be maintained at 100 mbar. For a given orifice size, increasing the pressure difference increases the mass flow rate which is proportional to the cooling capacity. The cooling fluid may be allowed to enter the feeder conduit non-forced, and the extraction be forced. Increasing the velocity of the air inflow increases the effectiveness of the cooling by breaking down boundary layers and enabling the cooling fluid to contact the heated surface. Not forcing the extraction prevents the drape being suctioned onto the robot arm.

The apparatus and methods described herein describe a cooling structure for a surgical robot arm which enables the temperature of the surface of the robot arm to be cooled to within the maximum safety temperature limits regardless of (i) the intensity of the manipulation of the robot arm, (ii) the length of time of the operation, and (iii) the fact that the robot arm is draped. Thus, during an operation, the operator is able to handle the robot arm, for example to change instruments or move the elbow out of the way, without exceeding the temperature limits.

Each loop described herein which circumscribes the surgical robot arm may be a continuous loop which forms a continuous closed path for the cooling fluid around the arm. Alternatively, each loop may be a discontinuous loop which forms a discontinuous closed path for the cooling fluid around the arm. For example, the loop may be a resilient closed horse-shoe shaped loop. This enables the operator to stretch the loop over the arm. When the operator releases the loop, it returns to the horse-shoe shape. Discontinuous closed path loops are particularly useful for those implementations in which the cooling structure is not integrated into the sterile drape. In those implementations which have multiple loops, one or more loop may be a continuous loop and one or more loop may be a discontinuous loop.

The drape and integrated cooling structure may be made of a flexible plastic such as polyester, polypropylene, polyethylene or polytetrafluoroethylene (PTFE).

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A cooling structure configured to cool a surgical robot arm, the surgical robot arm extending from a proximal end attached to a base to a distal end attachable to a surgical instrument via a series of links interspersed by articulations, the cooling structure comprising:
   a closed loop configured to circumscribe the surgical robot arm such that cooling fluid follows a continuous closed path around the surgical robot arm, the closed loop comprising:
      a hollow interior configured to feed cooling fluid through the closed loop, and
      a series of orifices directed towards the surgical robot arm configured to feed cooling fluid from the closed loop towards the surgical robot arm; and
   a feeder conduit attached to the closed loop configured to feed cooling fluid from a cooling fluid source to the closed loop.

2. A cooling structure as claimed in claim 1, wherein the series of orifices comprises orifices directed towards the distal end of the surgical robot arm.

3. A cooling structure as claimed in claim 1, wherein the series of orifices comprises orifices directed away from the distal end of the surgical robot arm.

4. A cooling structure as claimed in claim 1, wherein the closed loop has a uniform cross-section.

5. A cooling structure as claimed in claim 1, further comprising biasing projections attached to the closed loop, the biasing projections being directed towards the surgical robot arm, the biasing projections configured to contact the surgical robot arm so as to space the closed loop from the surgical robot arm.

6. A cooling structure as claimed in claim 1, further comprising one or more fasteners configured to fasten the cooling structure to the surgical robot arm.

7. A cooling structure as claimed in claim 1, further comprising one or more further loops configured to circumscribe the surgical robot arm, each further loop comprising:
a hollow interior configured to feed cooling fluid through the further loop, and
a series of further orifices directed towards the surgical robot arm configured to feed cooling fluid from the further loop towards the surgical robot arm.

8. A cooling structure as claimed in claim 7, wherein the feeder conduit is attached to each further loop in order to feed cooling fluid to that further loop, and wherein the feeder conduit spaces the closed loop and the one or more further loops apart from each other.

9. A cooling structure as claimed in claim 8, wherein the cooling structure is collapsible into a storage configuration in which the closed loop and the one or more further loops stack together.

10. A sterile drape configured to drape over a surgical robot arm comprising the cooling structure of claim 1.

11. A sterile drape configured to drape over a surgical robot arm comprising the cooling structure of claim 7, wherein the closed loop and the one or more further loops are separated by portions of drape.

12. A sterile drape as claimed in claim 10, wherein the closed loop joins together detached drape portions.

13. A surgical robot system comprising:
a surgical robot arm extending from a proximal end attached to a base to a distal end attachable to a surgical instrument via a series of links interspersed by articulations; and
a cooling structure configured to cool the surgical robot arm, the cooling structure comprising:
a closed loop configured to circumscribe the surgical robot arm such that cooling fluid follows a continuous closed path around the surgical robot arm, the closed loop comprising:
a hollow interior configured to feed cooling fluid through the closed loop, and
a series of orifices directed towards the surgical robot arm configured to feed cooling fluid from the closed loop towards the surgical robot arm; and
a feeder conduit attached to the closed loop configured to feed cooling fluid from a cooling fluid source to the closed loop; and
wherein the closed loop circumscribes the distal end of the surgical robot arm.

14. A surgical robot system comprising:
a surgical robot arm extending from a proximal end attached to a base to a distal end attachable to a surgical instrument via a series of links interspersed by articulations; and
a cooling structure configured to cool the surgical robot arm, the cooling structure comprising:
a closed loop configured to circumscribe the surgical robot arm such that cooling fluid follows a continuous closed path around the surgical robot arm, the closed loop comprising:
a hollow interior configured to feed cooling fluid through the closed loop, and
a series of orifices directed towards the surgical robot arm configured to feed cooling fluid from the closed loop towards the surgical robot arm; and
a feeder conduit attached to the closed loop configured to feed cooling fluid from a cooling fluid source to the closed loop; and
wherein the closed loop or one of one or more further loops circumscribes an articulation of the surgical robot arm.

15. A surgical robot system comprising:
a surgical robot arm extending from a proximal end attached to a base to a distal end attachable to a surgical instrument via a series of links interspersed by articulations; and
a cooling structure configured to cool the surgical robot arm, the cooling structure comprising:
a closed loop configured to circumscribe the surgical robot arm such that cooling fluid follows a continuous closed path around the surgical robot arm, the closed loop comprising:
a hollow interior configured to feed cooling fluid through the closed loop, and
a series of orifices directed towards the surgical robot arm configured to feed cooling fluid from the closed loop towards the surgical robot arm;
a feeder conduit attached to the closed loop configured to feed cooling fluid from a cooling fluid source to the closed loop; and
one or more fasteners configured to fasten the cooling structure to the surgical robot arm;
wherein the surgical robot arm further comprises one or more complimentary fasteners configured to fasten to the one or more fasteners of the cooling structure.

16. A method of cooling a surgical robot arm, the surgical robot arm extending from a proximal end attached to a base to a distal end attachable to a surgical instrument via a series of links interspersed by articulations, the method comprising:
forcing cooling fluid from a cooling fluid source through a feeder conduit to a closed loop which circumscribes the surgical robot arm such that cooling fluid follows a continuous closed path around the surgical robot arm; and
feeding the cooling fluid through a hollow interior of the closed loop and through a series of orifices directed towards the surgical robot arm.

17. A method as claimed in claim 16, further comprising extracting cooling fluid from the interior of the surgical robot arm.

18. A method as claimed in claim 17, comprising applying differential pressures to the cooling fluid forced into the feeder conduit and the cooling fluid extracted from the interior of the surgical robot arm.

* * * * *